US008361737B2

(12) United States Patent
Monif (10) Patent No.: US 8,361,737 B2
(45) Date of Patent: *Jan. 29, 2013

(54) FUIDI HERD MANAGEMENT SCHEMA

(76) Inventor: Gilles R. G. Monif, Bellevue, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/414,783

(22) Filed: Mar. 8, 2012

(65) Prior Publication Data

US 2012/0171689 A1     Jul. 5, 2012

Related U.S. Application Data

(63) Continuation of application No. 13/221,301, filed on Aug. 30, 2011, now Pat. No. 8,143,012, which is a continuation of application No. 12/287,822, filed on Oct. 15, 2008, now Pat. No. 8,008,033.

(51) Int. Cl.
*G01N 33/554*     (2006.01)
(52) U.S. Cl. ...................................... 435/7.32; 435/6.15
(58) Field of Classification Search .................. None
See application file for complete search history.

(56) References Cited

U.S. PATENT DOCUMENTS 7,422,869 B2    9/2008    Eda et al.

OTHER PUBLICATIONS

Nasher, S.A. et al. "Culture of *Mycobacterium avium* subspecies paratuberculosis (MAP) from the blood of patients with Crohn's disease: A Follow-Up Blind Multi Center Investigation" *The Open Inflammation Journal*, 2009, pp. 22-23, vol. 2.
Web site (temporary) idi.lpdesignsomaha.com: after Nov. 1, 2009, info@infectiousdiseasesincorporated.com.
Monif, G. et al., *10th International Colloquim on Paratuberculosis*, Minneapolis, MN, Aug. 9-14, 2009, p. 111.
Monif, G. "The FUIDI Herd Management Schema" *10th International Colloquim on Paratuberculosis*, Minneapolis, MN, Aug. 9-14, 2009, p. 141.
Dordhorst, N. et al. "Decision analysis model for paratuberculosis control in commercial dairy herds" *Preventive Veterinary Medicine*, 2006, pp. 92-122, vol. 75.
Collins, M. et al. "Evaluation of Five Antibody Detection Tests for Diagnosis of Bovine Paratuberculosis" *Clinical and Diagnostic Laboratory Immunology*, Jun. 2005, pp. 685-692, vol. 12, No. 6.
Williams, M. et at., The Paratuberculosis Newsletter, Mar. 2008, pp. 1, 2, 7 and 9.

*Primary Examiner* — Patricia A Duffy
(74) *Attorney, Agent, or Firm* — Saliwanchik, Lloyd & Eisenschenk (57) ABSTRACT

The invention is a herd management schema based upon the inventor's analysis of the natural history of bovine infection due to *Mycobacterium avium* subspecies *paratuberculosis* (Map) and related genomic variants and upon the ability of two distinct Map ELISA tests to sequentially or in parallel determine prior and current Map infection and evidence of active *mycobacterium* replication. Interpretation of the test results are integrated into sequential directives designed to enhance productive retention of infected animals as well as identify animals not previously infected. The sequential utilization of the data guidelines is developed to minimize the adverse economic impact.

3 Claims, 3 Drawing Sheets

FUIDI HERD MANAGEMENT SCHEMA

CROSS-REFERENCE TO RELATED APPLICATIONS

This application is a continuation of U.S. application Ser. No. 13/221,301, filed Aug. 30, 2011, which is a continuation of U.S. application Ser. No. 12/287,822, filed Oct. 15, 2008, now U.S. Pat. No. 8,008,033, the disclosures of which are hereby incorporated by reference in their entireties, including all figures, tables and amino acid or nucleic acid sequences.

FIELD OF INVENTION

The present invention is a business method/utility patent that integrates two types of serum ELISA tests for *Mycobacterium avium* subspecies *paratuberculosis* (Map) into a herd management schema that capitalizes on the natural history of Map infection.

DESCRIPTION OF PRIOR ART

The Disease

National Policy: Mycobacterium avium subspecies paratuberculosis (Map) is the causative agent of a chronic progressive granulomatous disease of the gastrointestinal tract, Johne's disease (Clarke 1997; Whitlock 1996). The organism is global in its distribution and causes disease in both wild and domestic herbivores. The granulomatous inflammation leads to diarrhea, cachexia, and eventual death (Clarke 1997; Raizman 2005). Infection with Map is increasing in prevalence among food-producing animals globally.

Economic Impact for the Dairy Industry: Estimates of herd prevalence using serological screening are comparatively low compared to the numbers achieved with fecal culture screening. Within large herds, up to 40% of cows may be infected (Chiodini 1983). Annual financial loss to the United States Dairy Industry alone is estimated at $220 million (Otts 1999).

Zoonotic Potential: Animal disease control programs have tended to focus on diseases with major economic impact, trade implication and/or zoonotic potential (Grant 2005). The zoonotic potential of Map may soon overshadow its annual adverse economical impact. In its progression from sub-clinical infection to disease, Map is introduced into the human food supply by virtue of its presence in milk. Map within milk is not adequately destroyed by pasteurization (Ayele 2005; Ellingson 2005; Giese 2000; Grant 2002; Miller 1996; Wuhib 2005).

*Mycobacterium bovis* is a documented zoonosis (Chiodini 1996; Herman-Taylor 1998). The organism is believed to pass from infected animals to man, primarily through oral ingestion of milk. The critical question regarding Map is not whether the organism is a zoonosis, but rather, in its dissemination to humans is Map etiologically linked to Crohn's disease.

A strong circumstantial case is developing which suggests that Map can function as a zoonotic pathogen with respect to Crohn's disease (Chiodini 1996; Mishina 1996; Naser 2000; Sechi 2001; Whittington 2000). Naser et al. isolated Map from the milk of two lactating women with Crohn's disease and none from five samples from normal control (Naser 2004).

Serum ELISA *Mycobacterium Avium* Subspecies *Paratuberculosis* Tests ELISA Test Sensitivity Two Map ELISA tests are in current use in the United States. The commercial Map ELISA tests, PARACHEK (Prionics, Zurich, Switzerland) and HERDCHEK (IDEXX Laboratories Inc. Westbrook, Me.) are based on the lipoarabinomannan polysaccharide (LAM) or other Map membrane related constituents. The Map strains used for diagnostic testing possess the IS 900 DNA insertion sequence. Map polymerase chain reaction (PCR) tests using primers derived from the IS900 gene sequence are used to confer specificity to suspected culture isolates. This insertion sequence is the principle means by which Map is differentiated from other *mycobacteria* (Sugden, Harris).

While there is a high degree of correlation between both types of commercial tests when done on clinically ill (fecal shedding, weight loss and diarrhea) animals, both types of Map ELISA tests fail to identify a significant number of fecal culture positive animals. The tests are used to identify negative, suspicious, and positive isolates. In terms of developing overt clinical disease, a sero-positive isolate has a positive predictive value of 74. A positive commercial Map ELISA test and/or fecal culture evidence of significant fecal shedding are the criteria (USDA's advocated policy of test-and-cull) in current use by which a decision is reached to remove a given animal from the herd (Harris). No diagnostic significance has been given to transient non-diagnostic values identified by either of the commercial Map ELISA tests. Despite the use of test-and-cull schema in herd management, the prevalence of Map in dairy herds has progressively increased. Sereologically positive, subclinically infected, as well as diseased dairy cows have been shown to shed Map into their milk and potentially introduce zoonotic pathogens into the human food chain.

Collins et al, evaluated five antibody detection tests for the diagnosis of bovine *paratuberculosis* using serum samples from 359 dairy cattle in seven *paratuberculosis*-free herds and 2,094 dairy cattle in seven Map-infected dairy herds. Both the PARACHEK and HERDCHEK (IDEXX) ELISA tests done in accordance with manufacturers' instruction and interpreted as prescribed by the kit insert, identified less than 29% of fecal culture positive cows. Linear regression analysis of quantitative results showed low correlation co-efficiency. Sockett et al. reported the sensitivity of commercial Elisa's for cattle to be 8.9 to 32.1% for low shedders and 47.1 to 62.9% for midlevel shedders. Sweeney et al. have suggested that commercial Elisa's might have a sensitivity rate lower than 13.5%. McKenna et al. tested sera collected from dairy cows at slaughter in assessing the agreement with documented infection of three commercially available Map ELISA tests which included HERDCHEK and PARACHEK. The investigators found a poor agreement between the three ELISA tests and infected cows. *Mycobacteria* have been shown to be more readily identified within feces when the currently commercially available Map ELISA tests are in their projected positive diagnostic zones (Cocito). The high incidence of false negatives with the PARACHEK and/or HERDCHEK ELISA tests has limited utility to identifying animals with an advanced disease state. A second concern with the membrane-based Map ELISA tests is the occurrence of false-positive test results.

Overall, the PARACHEK and HERDCHEK Map ELISA tests suffer from a lack of sensitivity in identifying animals with positive fecal cultures. Most claims of sensitivity have focused upon heavy shedding and/or clinically diseased animals. A suspicious or positive test did not necessarily predict outcome. The quest for antigenic specificity excluded the issue of genetic polymorphism within *Mycobaterium avium* subsp. *paratuberculosis* (Map).

A second type of Map ELISA test was developed utilizing primarily protoplasm from a *Mycobacterium* 18 that was initially thought to be Map but was later demonstrated to be more *Mycobaterium avium* than Map. Current data referable to the sensitivity of protoplasmic or whole organism antigen-based Map ELISA tests is lacking. While these tests identify diseased animals, they also produced a significant number of positive test results in animals that lacked confirmation by fecal culture or longitudinal clinical assessment. This fact significantly limited their utilization and virtual abandonment.

BRIEF DESCRIPTION OF THE DRAWINGS

FIG. 1—Part I of the FUIDI Herd Management Schema (FHMS) schematically presents the sequence of events when a diagnostic serum sample is submitted to a FUIDI certified veterinary diagnostic laboratory. The FUIDI test involves two Map ELISA tests that differ in their antigen spectrum and do not completely overlap. Both FUIDI#1 and FUIDI#2 tests are advocated, but cost considerations make sequential use more likely to be chosen with serum reanalysis with the FUIDI#2 test indicated only when FUIDI#1 has indicated serological evidence of current or prior significant B-cell stimulation. A negative Map FUIDI#1 test indicates that no evidence of Map directed B-cell stimulation is detected and the action advocated is to retest the animal annually. If the FUIDI#1 test is suspicious or positive, the serum sample is retested to assess the probability of active antigen processing. If the F1JIDI#2 test is negative, the recommended action is to retest the animal annually and/or after calving.

If a non-diagnostic or low titer is identified by the FUIDI#2 Map ELISA test, the interpretation is that a low-level ongoing infection is present. The vast majority of these animals will achieve immunological containment of *mycobacterium* replication. To assess, whether immune containment or progression towards disease is likely to ensue, the recommended action is to retest the animal using the FUIDI#1 and #2 Map ELISA tests in 3 months. If a diagnostic titer is identified, the interpretation is of high level *mycobacterium* replication. While the animal has about a 1 in 4 chance of achieving immunological containment, such an animal is, more likely than not a high fecal shedder of Map and should be culled. If a valuable animal or clinical parameter such as body score and milk/fat production are good, quantitative fecal culturing may provide valuable information for the information decision making.

FIG. 2—Part II of the FUIDI Herd Management Schema. Part II is designed to provide an additional level of monitoring to determine the probability of immunological containment versus progression of infection towards disease for a given animal. Fecal culturing of animals with high diagnostic FUIDI Test #2 results is reserved for uniquely valuable animals (bulls, valuable zoo animals) that have been isolated and for whom enhancement of their immune system is being implemented.

A fecal specimen is obtained for quantity assessment by direct fecal culture or by direct fecal nested or real-time Map polymerase chain reaction (PCR) tests. A negative culture indicates either immunological containment or sample error. The more probable demonstration indicates non-concurrence between serological data and organism shedding and warrants retesting of subsequent sera using FUIDI#2 Map ELISA test to see if serum titers decrease. If heavy fecal shedding is confirmed, the recommended action is to cull.

The key indicator as to prognosis is the diagnostic readings obtained upon serial FUIDI#2 testing. If the titer disappears or drops significantly, the potential for having Map in the milk, other than by contamination, is markedly reduced. If the FUIDI#2 titer remains relatively comparable, unless the animal's immune system is upregulated, the probability of progression to disease and Map shedding are theoretically enhanced. If the titer increases by 0.4 or greater, even though not in the test's diagnostic range, the recommended action is to cull.

Figure 1:
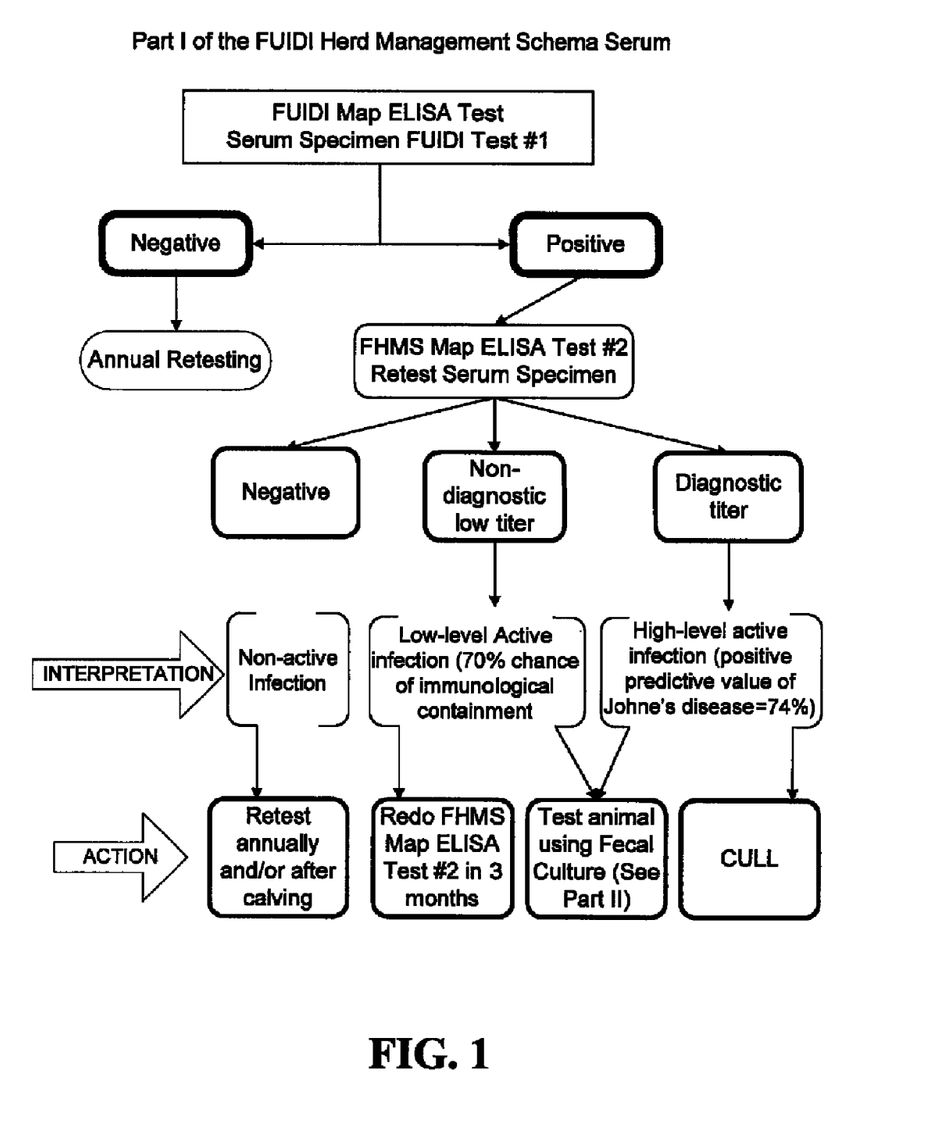
Figure 2:
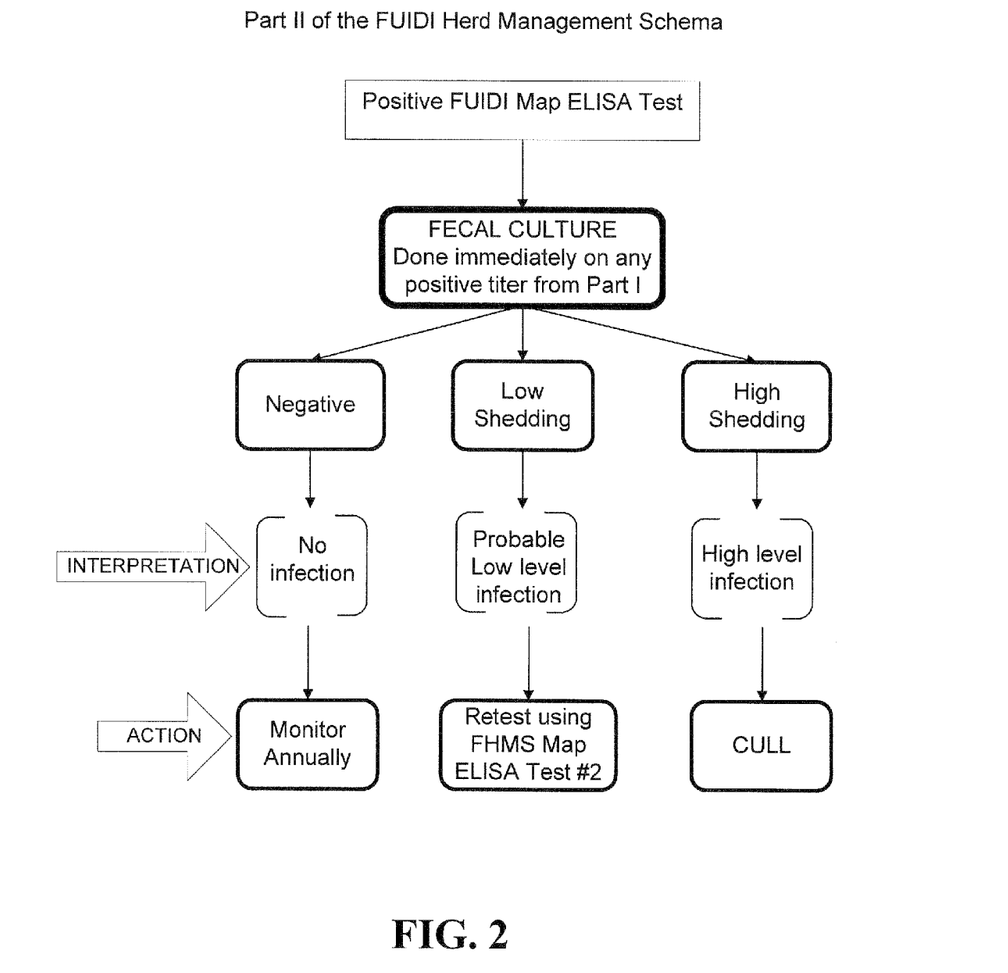
Figure 3:
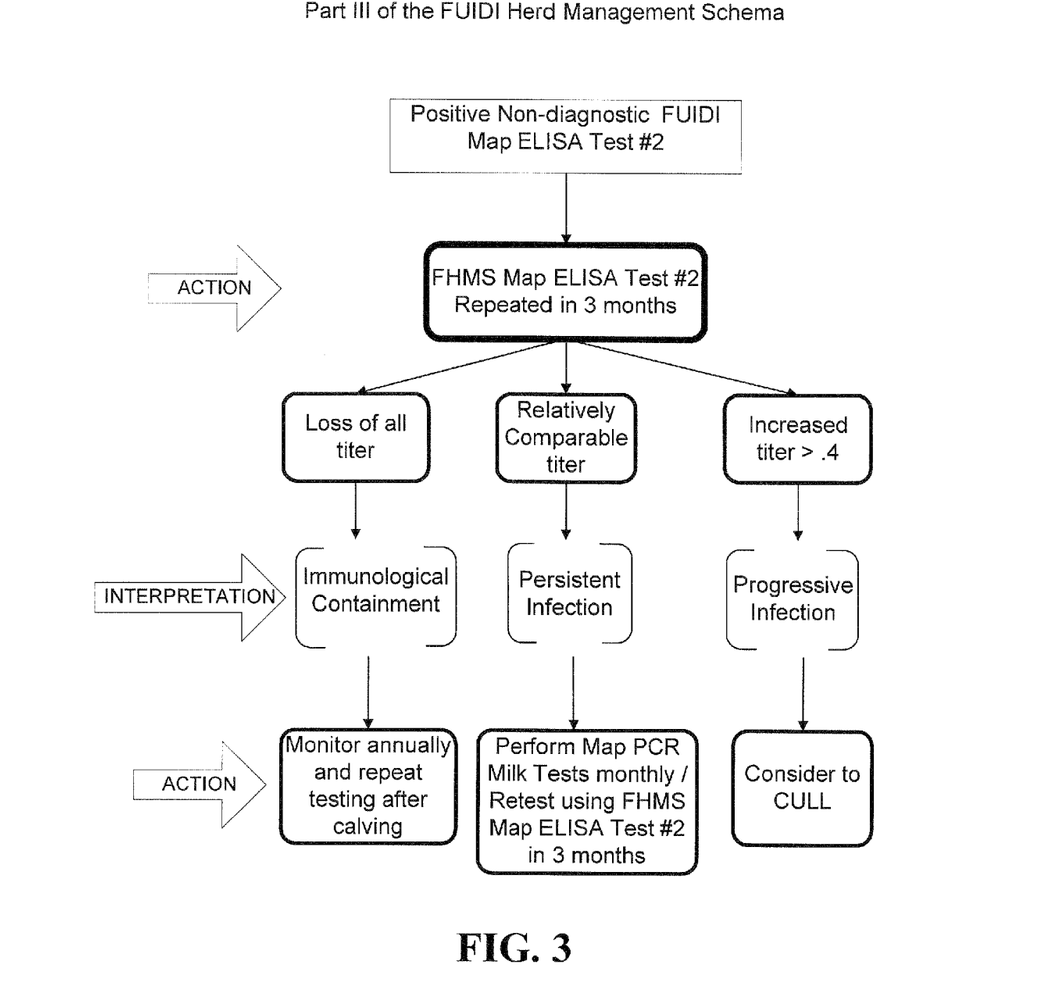
FIG. 3—Part III of the FUIDI Herd Management Schema focuses on animals that have had inferred active low level infection as determined the FUIDI #2 Map ELISA test. Production salvage of infected animals within this group is a key feature of the FUIDI Herd Management Schema.

It should be understood that the examples and embodiments described herein in FIGS. 1-3 are for illustrative purposes and that various modifications or changes in light thereof will be suggested to persons skilled in the art and are to be included within the spirit and purview of this application or embodiment thereof disclosed herein can be combined with any and/or all other elements or limitations (individually or in any combination) or any other invention or embodiment thereof disclosed herein, and all such combinations are contemplated to be within the scope of the invention without limitations.

DESCRIPTION OF THE INTELLECTUAL BASIS
OF THE INVENTION

Protoplasmic Antigen from *Mycobacterium* Species: FUIDI 1 (designated as "PTA-11837") was deposited with American Type Culture Collection (ATCC), P.O. Box 1549, Manassas, Va. 20108, on Apr. 18, 2011. The material has been deposited under conditions that assure that access to the material will be available during the pendency of this patent application to one determined by the Commissioner of Patents and Trademarks to be entitled thereto under 37 CFR 1.14 and 35 U.S.C. 122. The deposited material will be available as required by foreign patent laws in countries wherein counterparts of the subject application, or its progeny, are filed. However, it should be understood that the availability of a deposit does not constitute a license to practice the subject invention in derogation of patent rights granted by governmental action.

The invention is based upon re-defining existing data concerning Map ELISA tests in light of novel information derived by the inventor.

The existing information used was the antigenic base of the current commercial Map ELISA tests: the lipoarabinomannan polysaccharide (LAM) and/or related lipoprotein membrane constituents. This information was combined with the fact that these types of antigens tend to be of antibodies that are of relatively short duration compared with antibodies elicited by ribosomes and nucleic acid constituents.

Collaborative research done with United States Department of Agriculture, South Florida Dairy Herd Demonstration Project provides insight that alters perception of the natural history of Map infection. In a study of Map ELISA titers derived over a 14 month period, it was noted that approximately 10-11% of dairy cows would develop transient low level diagnostic antibodies which would disappear when retested. The literature infers the progressive nature of Map.

First, sixty-six sera were obtained from a North Florida dairy herd which had a high incidence of clinical disease. All tests were run in accordance with the manufacturers' specification. Positive and negative controls were utilized. Seven sera were identified as being positive by all three tests: six by the PARACHEK test, six by the HERDCHEK test, and seven by a protoplasmic-based ELISA test. The PARACHEK and IDEXX tests each failed to identify a positive sample identified by the other test. The higher the protoplasmic-based ELISA test registered, the greater the probability that the corresponding PARACHEK and/or HERDCHEK would be positive. The protoplasmic antigen-based test identified an additional 11 cows as having significant titer (14).

In an unpublished study, the FUIDI (a whole organism antigen base source) and PARACHEK Map ELISA tests were compared in parallel on the same serum specimen (Table 1-1). In Herd #1 that was reputedly Map-free, the PARACHEK ELISA test did not identify any serum specimens as being positive. The FUIDI ELISA test identified 10 animals as being infected. In Herd #2 that had a significant number of seroreactive cows, the PARACHEK ELISA identified 2 as being positive and 10 as being suspicious. The FUIDI ELISA test identified 16 as being positive and 3 as being suspicious.

This observation lead to the comparative use of a Map ELISA test whose antibody capturing capacity was dictated by LAM and a modified Map ELISA test (FUIDI) that identified antibodies to the protoplasmic mass antigens as well as surface membrane elements.

Significance of Diverging Map ELISA Test Results in Dairy Cows

Johne's disease is a chronic granulomatous disease of the bovine gastrointestinal tract caused by *Mycobaterium avium* subspecies *paratuberculosis* (Map) (1). The adverse economical impact of disease globally is estimated at 1.5 billion dollars annually (2).

The commercial Map ELISA tests have very poor sensitivity in identifying infected cows (3,4). Collins et al. evaluated five antibody detection tests for the diagnosis of bovine *paratuberculosis* using serum samples from 359 dairy cattle in seven *paratuberculosis*-free herds and 2,094 dairy cattle in seven Map-infected dairy herds (5). Both the PARACHEK (Prionics, Zurich, Switzerland) and HERDCHEK (IDEXX Laboratories Inc. Westbrook, Me.) ELISA tests done in accordance with manufacturers' instruction and interpreted as prescribed by the kit insert, identified less than 29% of fecal culture positive cows. Linear regression analysis of quantitative results showed a low correlation co-efficiency. Sockett et al. reported the sensitivity of commercial Elisa's for cattle to be 8.9 to 32.1% for low shedders and 47.1 to 62.9% for midlevel shedders (6). Sweeney et al. have suggested that commercial ELISAs might have a sensitivity rate lower than 13.5% (7). McKenna et al. tested sera collected from dairy cows at slaughter in assessing the agreement with documented infection of three commercially available Map ELISA tests which included HERDCHEK and PARACHEK. The investigators found a poor agreement between the three ELISA tests and infected cows (8). *Mycobacteria* have been shown to be more readily identified within feces when the currently commercially available Map ELISA tests are in their projected positive diagnostic zones (9).

A prior comparison of the IDEXX, PARACHEK and FUIDI Map ELISA #1 tests had shown excellent correlation between the three tests when the diagnostic criteria of either the IDEXX or PARACHEK tests were used to establish the denominator (12). Seven cows out of 66 cows were identified by all three tests: 6 by the PARACHEK test, 6 by the IDEXX tests and 7 by the FUIDI test. The IDEXX and PARACHEK tests each failed to identify a positive serum identified by the other. The FUIDI Map ELISA test identified 11 additional dairy cows as being infected with Map. The higher the FUIDI titer, the better the correlation was between the three tests. That is discrepancy between the FUIDI and commercial tests was not simply a case of over-diagnosis was inferred when the PARACHEK and FUIDI Map ELISA tests were tested against 9 sera from cows with necropsy confirmed Johne's Disease (13). In the PARACHEK Map ELISA test, four sera demonstrated any activity, but only one was positive and one was suspicious. In the prototype FUIDI test, six were positive. With the new diagnostic groupings for the FUIDI test, three would have been positive and three would have fallen in the suspicious category.

To achieve the mandated specificity indicative of only Map, the target antigens of the current commercial Map ELISA tests have had to be based upon a limited antigenic array such as the lipoarabinomannan or selected Map surface proteins. The serological response is a partial function of antigen complexity (10, 11). Different antigens elicit divergent types of antibodies. Whole organism antigenic utilization elicits an array of antibodies whose spectrum of reactivity exceeds that induced by subunits of the organism. By using a modified whole organism, the FUIDI test presents a significantly broader antigen array.

The purpose of this study is to analyze the possible significance of identification of any Map antibody titer by the PARACHEK Map ELISA test in conjunction with the corresponding FUIDI 41 Map titer and comment on the ramification derived from both tests as they apply to the natural history of bovine Map infection as opposed to Map disease.

Materials and Methods

Study Population:

Infectious Disease Incorporated (IDI) through its strategic partnership with the University of Florida College of Veterinary Medicine (UFCVM) was given access to sera and serological data derived from the 2008 USDA's Florida Johne's Disease Dairy Herd Demonstration Project (14). The study sera were determined for a given cow's serum having been tested by the State of Florida Diagnostic Laboratory in December of 2006 as well as February 2008 and its subsequent availability for retesting in 2008. The PARACHEK and FUIDI Map ELISA test results were derived by testing the same February 2008 serum samples.

PARACHEK Map ELISA Test: The PARACHEK Map ELISA tests were done at the State of Florida Diagnostic Laboratory-Live Oak in accordance to the manufacturer's instructions. Positive and negative controls were utilized. The test results were forwarded to the USDA's Office in Gainesville Florida. A suspicious reading was 0.50 to 0.99. A reading equal to or above one (1) was deemed positive.

Analysis of the PARACHEK Map ELISA data has presumed that the evidence presented to U.S. Department of Agriculture for commercial acceptance and certification had to have convincingly demonstrated that the test truly identifies antibodies specific to Map.

FUIDI Map ELISA #1 Test

The FUIDI Map ELISA test #1 uses primarily a modified antigen array based primarily on a Map isolate originally thought to be Map, but later been shown to be more *Mycobacterium avium*-like. Test sera were pre-absorbed with *Mycobacterium pheli*. ELISA results were calculated from absorbance at OD 405 nm. Readings less than 1.9 optical densities (OD) were deemed negative; readings between 1.9 and 2.4 were deemed as requiring close monitoring/suspicious. Readings of 2.5 OD or greater were called positive. All FUIDI Map ELISA #1 tests done at UFCVM were run in triplicate with both positive and negative controls. The test results were forwarded to the USDA's Office in Gainesville Fla.

Fecal Cultures: Fecal samples were shipped FedEx in coolers with ice packs to the Animal Disease Diagnostic Laboratory at Purdue University and processed according to that laboratory's internal protocols.

Data Processing:

The PARACHEK ELISA test results from the 2007 Florida Johne's Disease Dairy Herd Demonstration Project (testing done Dec. 13, 2006) were made available during the study. Once the final FUIDI Map test results had been submitted to USDA, the 2008 Florida Johne's Disease Dairy Herd Demonstration Project test results were forwarded for comparative analysis.

Statistical Analysis:

The random selection of the study sera which lacked specific targeted subgroups limited meaningful statistical analysis. For relative comparisons only, likelihood ratios (LR) were constructed for the FUIDI Map ELISA data to lend possible insight as to whether or not a FUIDI positive test result would predict a previously or concurrently Map dairy cow with Map specific antibodies. The LRs were calculated as follows: LR=(number of sera with a positive FUIDI Map ELISA test result divided by the number of sera which over approximately 14 months had been shown to have Map specific antibody; the number of positive and suspicious FUIDI ELISA tests divided by the number of PARACHEK sera which identified newly developed Map antibodies; the number of FUIDI-positive sera divided by the number of PARACHEK sera with Map antibodies at any time.

Results:

Of the 140 sera tested in February of 2008, 103 had been tested on December of 2006. In December of 2006, 10 of the 103 sera tested had any titer as measured by the PARACHEK Map ELISA test. Two were PARACHEK-positive and one serum was identified as being suspicious/inconclusive.

When reanalyzed in 2008, no data was available on one of the PARACHEK-positive animals (#2920; however, a strong positive titer was recorded in the FUIDI test (Table 2). One low PARACHEK titered cow (#1011) had its ELISA test values moved from 0.08 into the test's positive zone (2.38). Five previously low titered sera became totally negative.

Two cows had PARACHEK readings in the test's positive range. No follow-up PARACHEK test was done for cow #2920; however the high positive FUIDI reading is consistent with a continued high level of antigen processing. The other PARACHEK positive cow (#2290 exhibited a very significant drop in demonstrable Map antibodies (1.32 to 0.050). The suspicious PARACHEK serum similarly fell out of its diagnostic zone (0.72-0.02).

The remaining cow's serum maintained a persistent low Map antibody presence. Of these 11 sera which had any Map antibodies by the PARACHEK Map ELISA, 4 were positive and 3 were suspicious as determined by the FUIDI Map ELISA. The LR for the sera deemed positive in the FUIDI ELISA test is 0.40. If the suspicious and positive FUIDI results are combined, the FUIDI ELISA test's LR becomes 0.70.

Nine out of the 93 cows without prior Map antibodies in December 2006 developed low levels of Map antibodies when tested in February of 2008 (Table 3). The corresponding FUIDI tests were positive in two cases and suspicious in two others. The combined FUIDI positive and suspicious results create a LR of 0.56.

Table 4 reflects the shift of emphasis from PARACHEK directed comparisons to FUIDI directed comparisons. The FUIDI Map ELISA#1 test was positive in 12 instances. The presence of prior or concurrent Map antibodies as demonstrated by the PARACHEK Map ELISA test was identified in 8 instances.

Of the 21 animals postulated as requiring added surveillance/monitoring (suspicious category), six had prior or current identification of specific Map antibodies as identified by the PARACHEK ELISA and 4 of the 21 cows had a positive fecal culture. Combining the two criteria, prior demonstration of Map specific antibodies by the PARACHEK test and positive fecal cultures, approximately ⅓ of the cows in the FUIDI suspicious category had evidence of Map infection.

Two cows out of the 37 cows not previously tested in December of 2008 developed low levels Map antibody titer as determined by the PARACHEK test. For one of the two cows, the corresponding FUIDI test was positive.

Eleven cows had Map recovered from a fecal specimen (Table 5). Of the 11 Map positive fecal cultures, the PARACHEK test identified one as being positive in February 2008 (LR=0.09) The FUIDI identified in 2008 one as being positive and four as being suspicious (combined LR=0.36).

Discussion:

The primary focus of the comparison of the PARACHEK and FUIDI Map ELISA #1 tests was not to document that one test is necessarily better than the other, but rather to point out that these two ELISA tests do not necessarily convey the same information applicable to the natural history of bovine Map infection. When the 2008 suspicious and positive FUIDI Map ELISA #1 test results are compared with sera, in either 2007 or 2008, a sufficiently high correlation can be shown supporting the contention that the cows so identified as having any Map antibody titer in the PARACHEK test have experienced infection with Map. The overlapping correlation over time between a positive FUIDI ELISA titer and any titer PARACHEK ELISA test result strengthens the contention that any antibodies identified by the PARACHEK Map ELISA test are specific Map antibodies.

The FUIDI Map ELISA #1 was selected for development and testing predicated upon its ability to identify Map-like *mycobacteria* as well as Map. The rational for this decision was the contention that Map strains evolved from a *Mycobacteria avium* base and its genomic differentiation has resulted in genomic polymorphism of *mycobacterium* strains that are capable of inducing Johne's disease (14-24).

The FUIDI Map ELISA #1 test results can be challenged by the contention that they also identify environmental *mycobacteria*. Osterstock et al. parenterally immunized beef calves with *Mycobacterium celatinum, M. scrofulaceum, M. intracellulare,* and *M. avium* subspecies *avium* (25). False-positive ELISA tests were recorded with both commercial Map ELISA tests currently used in the United States. The authors contended that environment *mycobacteria* were responsible for some of the false positive tests previously observed in beef cattle. What they more probably demonstrated IS900 insertion sequence may share antigenic elements with selected environmental *mycobacteria*. The production of ELISA-positive antibodies directed against an environmental *mycobacterium* had required the subcutaneous injection with adjuvant of large numbers of organisms. In order to achieve a comparable PARACHEK-positive antibody response in nature would require organism internalization, antigen processing, and a large antigen mass: more specifically defined, infection.

In contrast to intracellular *mycobacteria*, the vast majority of pathogenic bacteria undergo complete organism elimination. In the course of disease, extremely high titers of antibodies directed against lipopolysaccharide and lipoprotein membrane components are produced; however their detection is relatively short-lived. The explanation advanced to account for disappearance of specific antibody titer has been that the eliciting antigenic templates are no longer available (27,28).

The appearance and disappearance of PARACHEK identified Map antibodies appears to be a direct function of the elicitor antigenic component used to develop the test. The PARACHEK Map ELISA test appears to be contingent upon continued processing of its antigenic elicitor for antibody production.

The loss of PARACHEK Map detectable antibodies implies that the host's immune response has achieved immunological governance. *Mycobacteria,* like *M. tuberculosis,* despite recovery, do not undergo complete elimination from the body. Evidence of an immune response persists years after the initial system introduction of the organism into the host animal (26). Reactivation of organism replication can occur when the host animal's immune system has undergone significant compromise (26).

By itself, the interpretation of data implying immune governance could be open to debate. What the FUIDI Map ELISA #1 data does lend is substantial credence to the contention that these animals which have lost PARACHEK titer have had or are experiencing a non-detectable level by the PARACHEK test infection with Map.

Epidemiologically, the small fragments of data relative to the loss of antibody titer directed against surface component of Map imply that a number of dairy cows infected with Map may achieve immunological governance. Fifty percent of the 10 cows with any Map antibodies had their titer in the PARACHEK test revert to a non-detectable titer upon retesting. Expansion of observations to an analysis of 602 dairy cows from which the 103 study sera were derived reveals that 46 of the 62 cows (75.8%) with previously identified Map antibodies lost all titer upon retesting.

A significant bias in the PARACHEK Map antibody group was the relative absence of animals identified by testing as being suspicious or positive. The herd's management schema dictated that serologically positive or suspicious cows, cows with significant fecal shedding, and/or cows with clinical signs be systematically culled from the herd. Nevertheless, three such animals were present in the study population: 2 test PARACHEK-positive and 1 PARACHEK-suspicious. Of the two PARACHEK-positive cows: one is inferred to have had a high level of antigen processing by the corresponding high positive FUIDI titer. The other positive cow had her PARACHEK titer drop from 1.32 to 0.05. Similarly, the suspicious cow's PARACHEK titer fell from 0.72 to 0.02. In both cases, the corresponding FUIDI titer was non-diagnostic.

The FUIDI Map ELISA #1 test appears to better identify the probability of either significant prior or current Map infection. The FUIDI antigenic base is constituted by a broad array of immunogens, some of which are theorized to persist along with evidence of specific cell-mediated immunity. Of the 10 sera with any positive antibody titer as determined by the PARACHEK done in December 2006, the FUIDI ELISA test was positive for 4 and suspicious for another 3, giving a combined LR of 0.7. Nine previously negative PARACHEK sera developed low levels of Map specific antibodies. The corresponding FUIDI titer was positive in 2 cases and suspicious in 2 of the 9 cases giving the combined group a LR of 0.56.

Of the 17 positive sera identified by the FUIDI Map ELISA #1 test, 6 identified cows that had or had evidence of specific Map antibodies as determined by the PARACHEK Map ELISA test (LR=0.35). If corrected to include a cow with positive fecal cultures the LR becomes 0.40.

Of the 21 suspicious FUIDI sera, 6 cows had or had had evidence of Map antibodies as determined by the PARACHEK Map ELISA test (LR=0.29). Two cows with no detectable Map antibodies, but suspicious in the FUIDI test were present.

For the cows with no detectable Map antibodies in 2007 and 2008, there is no way of accessing if in years prior to 2007 that they had not acquired Map infection with subsequent acquisition of immune governance which may account for some of the false positive FUIDI titers recorded.

The PARACHEK Map test appears to identify ongoing Map membrane antigen processing. The magnitude of the titer indicates the probability of future disease induction; however a diagnostic test does not necessarily predict future outcome. One PARACHEK-positive cow and one cow with a suspicious titer in 2007 when retested had insignificant residual titer in 2008.

From the Map ELISA test comparisons, any demonstration of Map specific antibodies by the PARACHEK Map ELISA test indicates systemic antigenic processing. The FUIDI-positive Map ELISA #1 test appears to identify both underlying as well as current Map infection. Like the PARACHEK test data, the FUIDI #1 test results cannot predict outcome, just probability. The FUIDI Map ELISA #1 test's utility appears to lie in its ability to better identify a subpopulation that could profit from more intensive monitoring.

From a parallel use of both ELISA tests, a better perception of the natural history of Map bovine infection is likely to emerge.

What is established from the cited data is that the transient positive titers identified by a LAM-based ELISA test were indicative of their Map specific antibodies. Their disappearance inferred that like, the human model, *Mycobacterium tuberculosis,* infection and immune capture are a common phenomenon and progression of infection to Johne's disease is a relative rarity.

The positive titers identified by protoplasmic antigen based tests are not false-positives but, with reasonable probability, identified prior Map infection (comparable to a positive PPD reaction to tuberculin), and the so-called false-positive tests observed with LAM-based Map ELISA tests are animals which subsequently achieved immune capture of the organism.

The novelty of the invention is how these new observations are used to create a comprehensive herd management schema which will allow domestic animal producers to better manage Map within their herd by retaining infected animals which by other criteria would be culled.

Prior to the development of the FUIDI Herd Management Schema, the gold standard was annual serological testing of animals using either the PARACHEK or I-IERDCHEK Map ELISA tests and/or fecal culture to determine if an animal should be removed from a herd for production considerations and/or for constituting a greater threat of introducing Map into the human food chain. The guidelines used in USDA's South Florida Dairy Herd Demonstration Program were:

Serological surveillance with a LAM-based Map ELISA test;

Fecal culture (elimination of significant shedders);

Clinical impression of disease; and

Significant decrease in milk and milk fat production.

This advocated approach is diseased focused and does not effectively use the now perceived natural history of Map infection nor the utility of dual surveillance within a Herd Management Schema to better identify infection with Map and determine the significance of a serological Map titer.

The FUIDI Herd Management Schema utilizes:

a serological single or multi-organism prototoplasm-based test to identify both current and past Map infection;

a LAM-based Map ELISA test to determine any degree of Map replication;

the fact that the majority of infected animals with low level and suspicious levels of Map antibodies will achieve subsequent immune capture to a varying degree;

the fact that 20-25% of animals with a diagnostic level of Map antibodies may also achieve subsequent immune capture;

the fact that animals with recent immune capture at the time of parturition may experience reactivation of infection; and the fact that majority of animals who are low Map fecal shedders and are serologically negative will exhibit subsequent immune capture.

The novelty in the information and its sequential utilization constitutes the basis for the invention and its claim to being a business method utility patent.

TABLE 1

Comparison of FUIDI and PARACHEK
Map ELISA tests
PARACHEK Comparison

| Source | Cow# | ELISA | PARACHEK |
|---|---|---|---|
| Dairy 1* | 8384 | 2.62 | Neg |
| Dairy 1 | 8661 | 2.61 | Neg |
| Dairy 1 | 8369 | 2.19 | Neg |
| Dairy 1 | 3721 | 2.46 | Neg |
| Dairy 1 | 3534 | 2.9 | Neg |
| Dairy 1 | 8291 | 1.94 | Neg |
| Dairy 1 | 8244 | 3.6 | Neg |
| Dairy 1 | 8064 | 2.08 | Neg |
| Dairy 1 | 8673 | 3.25 | Neg |
| Dairy 1 | 3119 | 2.11 | Neg |
| Dairy 1 | 7301 | 1.56 | Neg |
| Dairy 1 | 3238 | 1.46 | Neg |
| Dairy 1 | 6279 | 2.73 | Neg |
| Dairy 1 | 3815 | 1.65 | Neg |
| Dairy 1 | 8800 | 1.41 | Neg |
| Dairy 1 | 3361 | 1.22 | Neg |
| Dairy 1 | 2916 | 0.96 | Neg |
| Dairy 1 | 3405 | 1.4 | Neg |
| Dairy 1 | 7345 | 0.88 | Neg |
| Dairy 1 | 7659 | 0.58 | Neg |
| Dairy 1 | 3201 | 1.29 | Neg |
| Dairy 1 | 7519 | 0.63 | Neg |
| Dairy 1 | 3870 | 0.92 | Neg |
| Dairy 1 | 3520 | 0.65 | Neg |
| Dairy 1 | 7304 | 0.82 | Neg |
| Dairy 1 | 7658 | 0.61 | Neg |
| Dairy 1 | 3737 | 1.24 | Neg |
| Dairy 2* | 28 | 1.72 | Neg |
| Dairy 2 | 93 | 4.5 | Susp |
| Dairy 2 | 125 | 2.79 | Neg |
| Dairy 2 | 306 | 2.43 | Neg |
| Dairy 2 | 329 | 2.03 | Susp |
| Dairy 2 | 358 | 3.48 | Neg |
| Dairy 2 | 458 | 4.22 | Susp |
| Dairy 2 | 587 | 1.41 | Neg |
| Dairy 2 | 293 | 1.02 | Neg |
| Dairy 2 | 699 | 2.4 | Neg |
| Dairy 2 | 734 | 2.19 | Susp |
| Dairy 2 | 837 | 1.8 | Susp |
| Dairy 2 | 839 | 2.07 | Susp |
| Dairy 2 | 1260 | 2.67 | Susp |
| Dairy 2 | 1273 | 3.37 | Susp |
| Dairy 2 | 1514 | 6.57 | Pos |
| Dairy 2 | 1625 | 2.2 | Neg |
| Dairy 2 | 1718 | 4.87 | Susp |
| Dairy 2 | 1733 | 2.92 | Neg |
| Dairy 2 | 1581 | 1.72 | Neg |
| Dairy 2 | 2020 | 1.4 | Neg |
| Dairy 2 | 2075 | 0.95 | Pos |
| Dairy 2 | 1995 | 3.76 | Susp |

Dairy Herd #1 - reputedly Map-free
Dairy Herd #2 - known to have a significant # of sero-reactive cows
FUIDI values - 1.5 = negative; 1.51-1.99 = suspicious; 2.0 and above = positive

| Source | PARACHEK Positive/inconclusive | FUIDI positive/suspicious |
|---|---|---|
| Dairy Herd #1 | 0/0 | 10/0 |
| Dairy Herd #2 | 2/10 | 16/3 |

TABLE 2

Comparison of PARACHEK ELISA
Titers February 2008 with FUIDI ELISA
Titers on Sera with Pre-existing Map
Antibodies

| | PARACHEK | | |
|---|---|---|---|
| Cow # | Dec. 13, 2006 | Feb. 28, 2008 | FUIDI #1 |
| 1011 | .08 | 2.38 | 2.5 |
| 2290 | 1.32 | 0.05 | 1.0 |
| 2484 | 0.72 | 0.02 | 1.6 |
| 2920 | 1.42 | n.d. | 3.6 |
| 3125 | 0.02 | 0 | 3.3 |
| 3297 | 0.04 | 0 | 3.4 |
| 3728 | 0.08 | 0 | 2.1 |
| 3731 | 0.03 | 0 | 1.2 |
| 3739 | 0.09 | 0 | 1.97 |
| 3925 | 0.08 | .11 | 2.3 | n.d. = no data

TABLE 3

Comparative ELISA Titers between PARACHEK
and FUIDI Map ELISA Tests in Sera with Newly
Developed Map Antibodies

| | PARACHEK | | |
|---|---|---|---|
| Cow # | Dec. 13, 2006 | Feb. 28, 2008 | FUIDI #1 |
| 637 | n.d. | .06 | 3.1 |
| 1664 | 0 | .06 | 1.9 |
| 2139 | 0 | .02 | 1.6 |
| 2393 | 0 | .01 | 1.5 |
| 3111 | 0 | .03 | 2.0 |
| 3485 | 0 | .03 | 0.89 |
| 3523 | 0 | .01 | 1.1 |
| 3783 | 0 | .04 | 1.3 |
| 3790 | 0 | .02 | 2.0 |
| 3811 | 0 | .02 | 3.3 |
| 4259 | n.d. | .05 | 1.24 | n.d. = no data

TABLE 4

Correlation of FUIDI-positive Sera with Prior PARACHEK
Results

| | PARACHECK | | |
|---|---|---|---|
| Cow # | Dec. 13, 2006 | Feb. 28, 2008 | FUIDI #1 |
| | FUIDI #1 Titer (2.5 and greater) | | |
| 128 | 0 | 0 | 2.6 |
| 637 | n.d. | 0.06 | 3.1 |
| 1011 | 0.08 | 2.38 | 2.5 |
| 2109 | n.d | 0 | 2.9 |
| 2761 | n.d. | 0 | 3.2 |
| 2920 | 1.42 | n.d. | 3.6 |
| 3107 | 0.2 | 0 | 3.3 |
| 3297 | 0.04 | 0 | 3.4 |
| 3387 | n.d. | 0.05 | 3.4 |
| 3536 | n.d. | 0 | 2.9 |

TABLE 4-continued

Correlation of FUIDI-positive Sera with Prior PARACHEK Results

| | PARACHECK | | |
|---|---|---|---|
| Cow # | Dec. 13, 2006 | Feb. 28, 2008 | FUIDI #1 |
| 3811 | 0 | 0.02 | 3.3 |
| 3945 | 0 | 0.05 | 3.4 | n.d. = no data

TABLE 5

Correlation of FUIDI-Positive and -Suspicious MAP ELISA Titers with Any PARACHEK Titer

| | | PARACHEK Titer | |
|---|---|---|---|
| Cow # | FUIDI ELISA #1 | Dec. 13, 2006 | Feb. 28, 2008 |
| FUIDI #1 Titer (2.5 and greater) | | | |
| 128 | 2.6 | 0 | 0 |
| 637* | 3.1 | — | 0.06 |
| 1011 | 2.5 | 0.08 | 2.38 |
| 1663 | 2.9 | 0 | 0 |
| 2109 | 2.9 | | 0 |
| 2674 | 3.3 | — | — |
| 2761 | 3.2 | | 0 |
| 2920 | 3.6 | 1.42 | — |
| 3107 | 3.3 | 0.2 | 0 |
| 3160 | 2.6 | 0 | 0 |
| 3297 | 3.4 | 0.04 | 0 |
| 3536 | 2.9 | 0 | 0 |
| 3702 | 2.5 | 0 | 0 |
| 3811 | 3.3 | 0 | 0.02 |
| 3945 | 3.4 | 0 | 0.05 |
| 3387 | 3.1 | — | 0 |
| 4320 | 2.6 | — | 0 |
| FUIDI #1 Titer (1.9-2.49) | | | |
| 480 | 2.3 | | n.d |
| 1004 | 2.1 | | 0 |
| 2676 | 2.3 | | 0 |
| 2891 | 2.0 | | 0 |
| 3103 | 2.0 | | 0 |
| 3111 | 2.0 | | 0.03 |
| 3611 | 2.12 | | 0 |
| 3621 | 2.1 | | 0 |
| 3652 | 1.9 | | 0 |
| 3728 | 2.1 | 0.08 | 0 |
| 3735 | 2.3 | | 0 |
| 3739 | 1.97 | 0.09 | 0 |
| 3763 | 2.1 | | 0 |
| 3790 | 2.0 | | 0.02 |
| 3925 | 2.3 | 0.08 | 0.11 |
| 3953 | 2.1 | | 0 |
| 4115 | 1.9 | | 0 |
| 4194 | 2.1 | | 0.02 |
| 4212 | 1.9 | | 0 |
| 4314 | 2.1 | | 0 |
| 4471 | 2.3 | | 0 | n.d. = no data

TABLE 6

Correlation of PARACHEK and FUIDI Map ELISA Titers with Positive Fecal Cultures

| Cow # | PARACHEK ELISA 2008 | FUIDI ELISA #1 2008 | Culture |
|---|---|---|---|
| 1011 | 2.38 (positive) | 2.5 (positive) | ls |
| 3160 | 0 | 2.16 (suspicious) | ms |
| 4156 | 0 | 1.3 (negative) | ls |

TABLE 6-continued

Correlation of PARACHEK and FUIDI Map ELISA Titers with Positive Fecal Cultures

| Cow # | PARACHEK ELISA 2008 | FUIDI ELISA #1 2008 | Culture |
|---|---|---|---|
| 4237 | 0 | 1.4 (negative) | ls |
| 3394 | 0 | 1.6 (negative) | ms |
| 4101 | 0 | 1.1 (negative) | ms |
| 4115 | 0 | 1.9 (suspicious) | ms |
| 4194 | 0.02 | 2.1 (suspicious) | hs |
| 4212 | 0 | 1.9 (suspicious) | ms |
| 4235 | 0 | 1.3 (negative) | ls |
| 4237 | 0.01 | 1.3 (negative) | ms | ls = light shedder
ms = medium shedder
hs = heavy shedder

REFERENCES

1. Stabel J. R.: Johne's disease: a hidden threat. J. Dairy Science 1998; 81:283-288
2. Chi J., Van Leeuwen J. A., Weersink A., Keefe G. P.: Direct production loses and treatment costs from bovine viral diarrhea virus, bovine leucosis virus *Mycobaterium avium* subsp. *paratuberculosis* and *Neospora caninum*. Prevent. Vet. Med. 2002; 69:2075-2082
3. Eamens G J, Whittington R J, Marsh I B, Turner M J, Saunders V, Kemsley P D, Rayward D: Comparative sensitivity of various fecal culture methods and ELISA in dairy cattle herds with endemic Johne's disease. Vet. Microbiol. 2000; 77:357-367
4. Sweeney R W, Whitlock R H, Buckley C L, Spencer P A: Evaluation of a commercial-linked enzyme immunosorbent assay for the diagnosis of *paratuberculosis*. J. Vet. Diagn. Invest. 1995; 7:488-493
5. Collins M. T., Wells S. J, Petrini K. R. et al.: Evaluation of five antibody detection tests for the diagnosis of bovine *paratuberculosis*. Clin. Diagn. Immunol. 2005; 12: 685-692
6. Sockett D. C., Conrad T. A., Thomas C. B., Collins M. T.: Evaluation of four serological tests for bovine *paratuberculosis*. J. Clin, Microbiol. 1992; 30:1134-1139
7. Sweeney R. W., Whitlock R. H., McAdams S., Fyock T.: Longitudinal study of ELISA seroreactivity to *Mycobaterium avium* subspecies *paratuberculosis* in infected cattle and culture-negative herd mates. J. Vet. Diagn. Invest. 2006; 18:2-6
8. McKenna S. L. B., Barkema H. W., Keefe G. P., Sockett D. C.: Agreement between three Elisa's for *Mycobaterium avium* subsp. *paratuberculosis* in dairy cattle. Vet. Microbiol. 2006; 31:285-291
9. Cocito C., Gilot P., Coene M. de Kesel M., Poupart P., Vannuffel P.: Paratuberculosis. Clin. Microbiol. Review 1994; 7:328-345
10. Collins M. T., Wells S. J., Petrini K. R. Collins J E, Schultz R D, Whitlock R H.: Evaluation of five antibody detection tests for diagnosis of bovine *paratuberculosis*. Clin. Diagn. Immunol. 2005: 12:685-692
11. Collins M. T., Gardner I. A., Garry F. B., Roussel A. J., Wells S. J.; Consensus recommendations on diagnostic testing for the detection of *paratuberculosis* in cattle in the United States. J. Am. Vet. Med. Assoc. 2006; 229:1912-1918
12. Williams E., Monif, G. R. G., Buergelt C. D.: Comparative analysis of different Map ELISA tests. The *Paratuberculosis* Newsletter March 2008:7

13. Williams E., Monif G. R. G.: Comparative Map ELISA tests done on cows with necropsy documented disease. The Paratuberculosis Newsletter. March 2008: 7-8
14. Harrell C. D., Gauthier J., Berman W.: Unpublished data.
15. Herman-Taylor J., Bull T. J., Sheriden J. M.: Causation of Crohns disease by *Mycobaterium avium* subspecies *paratuberculosis*. Canadian J. Gastroenteriol. 2001; 14:521-527
16. Whittington R., Marsh I., Chow E., Cousins D.: Polymorphism in IS1311, an insertion sequence common to *Mycobaterium avium* subsp. *paratuberculosis*, can be used to distinguish between and within these species. Mol. Cell. Probes 1998; 12: 349-358
17. England S., Bolske G., Johnansson K. E.: An IS900-like sequence found in *Mycobacterium sp.* other than *Mycobacterium avium* subspecies *paratuberculosis*. FEMS Microbiol. Lett. 2002; 34:734-737
18. Tasara T., Hoelzle L. E., Stephan R.: Development and evaluation of a *Mycobaterium avium* subspecies *paratuberculosis* (MAP) specific multiplex PCR assay. Int. J. Food Microbiol 2005; 104:279-287
19. Bolski G, Johansson K. E.: An IS900-like sequence found in a *Mycobacterium sp.* other than *Mycobaterium avium* subspecies *paratuberculosis*. FEMS Microbiol. Lett. 2002; 209:267-271
20. Cousins D. V., Whittington R., Marsh I. Masters R. J., Evans R. J., Kluver P.: *Mycobacteria* distinct from *Mycobaterium avium* subspecies *paratuberculosis* isolated from feces of ruminants posses IS900-like sequences detectable by polymerase chain reaction: implications for diagnosis. Mol. Cell. Probes1999; 14:431-442
21. Coffin J. W. C., Condon C. A., Compston K. N. et al: Use of restriction fragment length polymorphisms resolved by pulsed-field gel electrophoresis for subspecies identification of *mycobacteria* in the *Mycobacterium avium*-complex and for isolation of DNA probes. J. Clin. Microbiol. 1992; 30:1829-1836
22. Makeda S., Turenne C. Y., Behr M. A.: Insertion Sequence IS900 revisited. J. Clin. Microbiol. 2006; 44:1081-1083
23. Fridriksdottir V., Gunnarsson E., Sigurdarson G., Gudmundsdottir K. B.: *Paratuberculosis* in Iceland: epidemiology, control measures past and present. IN Manning E. J. B. and Collins M. T (Eds.) Proceedings of the Sixth Colloquium on *Paratuberclosis*, 1999, Melbourne, Australia, February 14-18, pp.105-108
24. Whittington R. J., Targel C. A., Ottaway S., Marsh I., Seaman J., Fridriksdottir V.: Molecular epidemiological confirmation and circumstances of occurrence of sheep (S) strain of *Mycobaterium avium* subsp. *paratuberculosis* in cases of *paratuberculosis* in cattle in Australia and sheep and cattle in Iceland. Vet. Microbiol. 201; 79:311-32
25. Osterstock J. B., Fosgate G. T., Norby, B. Manning E. J. B. Collins M. T., Roussel A. J.: Contributions of environmental *mycobacteria* to false-positive serum ELISA results for *paratuberculosis*. J. Am. Vet. Med. Assoc. 2007; 230:896-901
26. Daley J, W, Monif, G. R. G. in Infectious Diseases in Obstetrics and Gynecology. 6th edition 2008, Gilles R. G. Monif and David Baker (Eds.). Informa, Andover Hampshire, UK. pp 318-330
27. Tizard I. R.: Acquired Immunity: Antigen-Presenting Receptors. In Veterinary Immunology, Ian R. Tizard editor. 7$^{th}$ edition, pp. 67-77. Elsevier, Philadelphia, Pa.
28. Tizard I. R.: Acquired immunity to bacteria and related organisms. In Veterinary Immunology, Ian R. Tizard editor. 7th edition. Chapter 23, pp. 273-276. Elsevier, Philadelphia, Pa.
29. Ayele W. Y., Svastova P., Roubal P., Bartos M, Pavlik I.: *Mycobacterium avium* subspecies *paratuberculosis* cultured from locally and commercially pasteurized cow's milk in the Czech Republic. Appl. Envir. Microbiol. 71:1210-1214, 2005
30. Clarke C. J. The pathology and pathogenesis of *paratuberculosis* in ruminants and other species. J. Comp. Pathol. 116:217-261, 1997
31. Chiodini R. J., Van Kruiningen H. J., Merkal R. S.: Ruminant *paratuberculosis* (Johne's disease): the current status and future prospects. Cornell Vet. 74:218-262, 1984
32. Chiodini R. J., Rossiter C. A.: *Paratuberculosis:* A potential zoonosis.: Vet. Clin. North America: Food Animal Practices 12:457-467, 1996
33. Ellingson J. L., Anderson J. L., Koziczkowski J. J., Radcliff R. P., Sloan S. J., Allen S. E., Sullivan N. M.: Detection of viable *Mycobacterium avium* subspecies *paratuberculosis* in retail pasteurized whole milk by two culture methods and PCR. J. Food Prot. 68:966-972, 2005
34. Giese S. B., Ahrens P.: Detection of *Mycobaterium avium* subsp. *paratuberculosis* in milk from clinically affected cows by PCR and culture. Vet. Microbiol. 77:291-297, 2000
35. Grant I. R., Ball H. J., Rowe M. T.: Incidence of *Mycobacterium paratuberculosis* in bulk raw and commercially pasteurized milk from approved dairy processing establishments in the United Kingdom. Appl. Envir. Microbiol. 68:2428-2435, 2002
36. Grant I. R.: Zoonotic potential of *Mycobaterium avium* subsp. *paratuberculosis:* the current problem. J. Appl. Microbiol. 98:1292-1290, 2005
37. Hermon-Taylor J., Barnes N., Clarke C., Finlayson C.: Grand Rounds *Mycobacterium paratuberculosis* cervical lymphadenitis, followed five years later by terminal ileitis similar to Crohn's disease. British Med. J.316b:449-453, 1998
38. Millar D., Ford J., Sanderson J., Withey S., Tizard M., Doran T., Hermon-Taylor J.: IS900 PCR to detect *Mycobaterium avium* subspecies *paratuberculosis* in retail supplies of whole pasteurized milk in England and Wales. Appl. Environ Microbiol. 62:3446-52, 1996
39. Mishina D., Katsel P., Brown S. T. Gilberts C. A. M., Greenstein R. J.: On the etiology of Crohn's disease. Proc. Natl. Acad. Sci. USA 93:9816-20, 1996
40. Naser S. A., Schwartz D., Shafran I.: Isolation of *Mycobaterium avium* subsp. *paratuberculosis* from breast milk of Crohn's disease patients. Am. J. Gastroentereol; 95:1094-1095, 2000
41. Naser S. A., Ghobrial G., Pomero C., Valentine J. F.: Culture of *Mycobacterium avium* subspecies *paratuberculosis* from the blood of patients with Crohn's disease. Lancet 364:1039-1044, 2004
42. Ott S. L., Wells S. J., Wagner B. A.: Herd-level economic losses associated with Johne's disease on US dairy operations. Prev. Vet. Med. 40:179-192, 1999
43. Raizman E. A., Wells S. J., Jordan P. A., DelGiudice G. D., Bey R. R.: *Mycobacterium avium* subsp. *paratuberculosis* from free-ranging deer and rabbits surrounding Minnesota dairy herds. Can. J. Vet. Res. 69:32-38, 2005
44. Sechi L. A., Mura M., Tanda F. Amelia L, Antonello S, Fadda G, and Zanetti S.: Identification of *Mycobacterium avium* subsp. *paratuberculosis* in biopsy specimens from patents with Crohn's disease. J. Clin. Microbiol. 39:4514-17, 2001
45. Sechi L. A., Mura M., Tanda F. Amelia L, Antonello S, Fadda G, and Zanetti S.: Identification of *Mycobaterium*

*avium* subsp. *paratuberculosis* in biopsy specimens from patients with Crohn's disease. J. Clin. Microbiol. 39:4514-17, 2001
46. Whitlock R. H., Buergelt C. D.: Preclinical and clinical manifestations of *paratuberculosis* (including pathology). Vet. Clin. N. Am. 12:357-371, 1996
47. Whittington R J, Hope A F, Marshall A. D.: Molecular epidemiology of *Mycobaterium avium* subsp. *paratuberculosis:* IS900 restriction fragment length polymorphism and IS 1311 polymorphism analysis from animals and a human in Australia J. Clin. Microbiol 38:3240-3248, 2000
48. Wuhib Y. A., Svastova P., Roubal P., Artos M., Paylik I.: *Mycobacterium avium* subspecies *paratuberculosis* cultured from locally and commercially pasteurized cow's milk in the Czech Republic. Appl. Environ Microbiol. 71:1210-1214, 2005
49. Cocito C., Gilot P., Coene M. de Kesel M., Poupart P., Vannu fel P.: *Paratuberculosis*. Clin. Microbiol. Review 1994; 7:328-345
50. Collins M. T., Wells S. J, Petrini K. R. et al.: Evaluation of five antibody detection tests for the diagnosis of bovine *paratuberculosis*. Clin. Diagn. Immunol. 2005; 12: 685-692
51. Harris N. B., Bareletta R. G.: *Mycobaterium avium* subsp. *paratuberculosis* in Veterinary Medicine. Clin. Microbiol Reviews 2001;14:489-512
52. McKenna S. L. B., Barkema H. W., Keefe G. P., Sockett D. C.: Agreement between three Elisa's for *Mycobacterium avium* subsp. *paratuberculosis* in dairy cattle. Vet. Microbiol. 2006; 31:285-291
53. Sockett D. C., Conrad T. A., Thomas C. B., Collins M. T.: Evaluation of four serological tests for bovine *paratuberculosis*. J. Clin. Microbiol. 1992; 30:1134-1139
54. Sugden E. A., Stilwel K., Michaelides A.: A comparison of lipoarabinomannan with other antigens used in the absorbed enzyme immunoassay for serological detection of cattle infected with *Mycobacterium paratuberculosis*. J. Vet. Diagn. Invest. 1997; 9:413-417
55. Sweeney R. W., Whitlock R. H., McAdams S., Fyock T.: Longitudinal study of ELISA seroreactivity to *Mycobaterium avium* subspecies *paratuberculosis* in infected cattle and culture-negative herd mates. J. Vet. Diagn. Invest. 2006;18:2-6
56. Williams E., Monif G. R. G., Buergelt C. D.; Comparative analysis of different Map ELISA tests. The *Paratuberculosis* Newsletter. March 2008:9-10

I claim:

1. A method of managing an animal herd comprising identifying prior or current infection/disease in an animal caused by *Mycobacterium avium* subspecies *paratuberculosis* (MAP) and genomically related *mycobacteria* comprising:
   a) conducting an initial serological ELISA test to identify intracellular antigens of MAP and genomically related *mycobacteria*, said serological ELISA test comprising contacting serum from an animal with FUIDI antigen and detecting the binding of antibodies to said FUIDI antigen, said FUIDI antigen deposited as ATCC PTA-11837, said managing comprising categorizing animals in said herd by designating an animal as being negative or positive for the presence of antibodies binding said FUIDI antigen in said initial serological ELISA test; and
   b) conducting a second serological ELISA test on an animal categorized as positive as positive for the presence of antibodies binding to said FUIDI antigen to identify intracellular antigens of MAP and genomically related *mycobacteria*, said second serological ELISA test comprising contacting serum collected from said animal categorized as positive for the presence of antibodies binding to lipoarabinomannan polysaccharide (LAM) antigen and detecting the binding of antibodies to said LAM-antigen and said managing comprising further testing of said animal for the presence of MAP nucleic acids from a fecal sample or culling said animal from a herd if said second serological ELISA test is positive for antibodies binding said LAM antigen or returning said animal to the herd if said animal is negative for the presence of antibodies binding said LAM antigen in said second serological ELISA test.

2. The method according to claim 1, wherein said animal categorized as negative for the presence of antibodies binding said LAM antigen is retested annually or after calving.

3. The method according to claim 1, further comprising conducting a PCR assay on a fecal sample from said animal positive for the presence of antibodies binding to FUIDI antigen and LAM antigen to determine the presence or absence of nucleic acids from MAP, and culling said animal from the herd if positive for the presence of MAP nucleic acids, or returning said animal to the herd of negative for the presence of MAP nucleic acids.

* * * * *

UNITED STATES PATENT AND TRADEMARK OFFICE
CERTIFICATE OF CORRECTION

PATENT NO. : 8,361,737 B2
APPLICATION NO. : 13/414783
DATED : January 29, 2013
INVENTOR(S) : Gilles R. G. Monif It is certified that error appears in the above-identified patent and that said Letters Patent is hereby corrected as shown below:

In the Claims:

Column 18,
Line 5, "*mycobacteria* comprising:" should read --mycobacteria comprising:--

Line 8, "related *mycobacteria*," should read --related mycobacteria,--

Line 17, "as positive as positive" should read --as positive--

Line 20, "related *mycobacteria*," should read --related mycobacteria,--

Line 29, "binding said" should read --binding to said--

Signed and Sealed this
Seventh Day of May, 2013

Teresa Stanek Rea
*Acting Director of the United States Patent and Trademark Office*